United States Patent [19]

Maupetit et al.

[11] 4,064,060

[45] Dec. 20, 1977

[54] EPOXY ALCOHOL TRICYCLIC NORSESQUITERPENE DERIVATIVE AND COMPOSITIONS CONTAINING THE SAME

[75] Inventors: Pierre Maupetit; Paul Jose Teisseire, both of Grasse, France

[73] Assignee: Societe Anonyme Roure Bertrand Dupont, Paris, France

[21] Appl. No.: 723,749

[22] Filed: Sept. 16, 1976

Related U.S. Application Data

[63] Continuation-in-part of Ser. No. 444,684, Feb. 21, 1974, Pat. No. 4,000,202.

[30] Foreign Application Priority Data

Feb. 28, 1973 Switzerland .......................... 2884/73
July 3, 1973 Switzerland .......................... 9723/73

[51] Int. Cl.$^2$ .......................... C11D 9/04; C11B 9/00; A61K 7/46
[52] U.S. Cl. .................................. 252/89 R; 252/108; 252/522; 252/550; 260/348.52; 424/278; 424/283; 424/285
[58] Field of Search .......................... 252/89, 522, 108; 260/348 C, 348 R; 424/278, 283, 285, 550

[56] References Cited

U.S. PATENT DOCUMENTS 4,000,202   12/1976   Maupetit et al. ................ 252/522 X

*Primary Examiner*—Mayer Weinblatt
*Attorney, Agent, or Firm*—Wallenstein, Spangenberg, Hattis & Strampel

[57] ABSTRACT

Odoriferous agent in the form of a novel epoxyalcohol tricyclic norsesquiterpene derivative having the formula

III

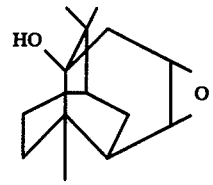

4 Claims, No Drawings

EPOXY ALCOHOL TRICYCLIC NORSESQUITERPENE DERIVATIVE AND COMPOSITIONS CONTAINING THE SAME

This application is a continuation-in-part of application Ser. No. 444,684, filed Feb. 21, 1974, now U.S. Pat. No. 4,000,202, dated Dec. 28, 1976.

This invention is concerned with a novel epoxyalcohol tricyclic derivative having the formula

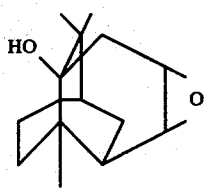

III

The foregoing compound has been found to be useful as an odorant and it is additionally useful as an intermediate for the preparation of other odorants. It also possesses fixative properties. Its odor may be described as being camphorous, musty and woody. It can be combined in a manner known per se with other odorants to give particular odorant compositions (for example perfume bases), whereby the content of said compounds in such odorant compositions may vary within wide limits, for example between about 1 and 20 wt.%. Such odorant compositions can be used as perfumes or for the perfuming of cosmetic products (soaps, toilet waters, creams, etc.) as well as, for example, cleaning agents (detergents, washing agents, etc.).

The foregoing compound III is prepared by subjecting the unsaturated tricyclic alcohol norpatchoulenol (nordehydropatchoulol) of the following formula II to epoxidation.

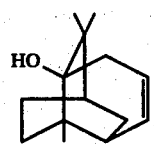

II

The unsaturated tricyclic alcohol (nordehydropatchoulol or norpatchoulenol), which serves as the starting material for the manufacture of the formula III compound, is present in natural patchouli oil and can be isolated therefrom by known methods (c.f. French Pat. No. 7,131,577).

The epoxidation of norpatchoulenol II to produce the epoxy alcohol III can be carried out using a peracid such as perphthalic acid, perbenzoic acid or peracetic acid. The latter is preferred because of its ready availability.

The invention will now be illustrated with reference to the following Examples

EXAMPLE 1

Preparation Of Compound Of Formula III 1 g (4.8 mmol) of norpatchoulenol, dissolved in 50 ml of methylene chloride, and 1 g of dry sodium acetate are added to a 500 ml flask. The thus obtained suspension is stirred vigorously, cooled and then mixed with 15 ml of 35% peracetic acid. The mixture is then left for 48 hours at room temperature, until the norpatchoulenol has practically disappeared. After the addition of 300 ml of water, the reaction mass is extracted with methylene chloride. Then the organic extracts are washed with 9% sodium bicarbonate solution, 10% sodium sulphite solution and finally to neutrality with water. The solvent is then distilled off. There are thus obtained 1.05 g of crystallised, crude epoxyalcohol of the formula III, which can be obtained analytically pure (90% yield) by chromatography on silica gel and vacuum sublimation and then shows the following constants:

$[\alpha]_D^{25}(CHCl_3) = +29.7°$.

Mass Spectrum: $C_{14}H_{22}O_2$ (M = 222). 222(M); 207 (M—$CH_3$); 204 (M—$H_2O$); 189 (M—$H_2O$—$CH_3$); 179 (M—$C_3H_7$); 166; 161 (M—$H_2O$—$C_3H_7$); 138; 95; 84.

IR-Spectrum: $\nu_{max}^{KBr}$(cm$^{-1}$): 3520; 3620; 3460; 3000; 1465; 1380–1365; 1305; 1060–1040; 1030; 980; 950-870–810; 755; 740.

NMR-Spectrum: (in δ units) 0.89; 1.01; 1.11; 2.80; 3.01.

The use of the compound of formula III as an intermediate for the production of other compounds having odorant properties of a camphorous, musty and woody character is illustrated by the following Reaction scheme and exemplified by Examples 2 and 3.

Reaction Scheme

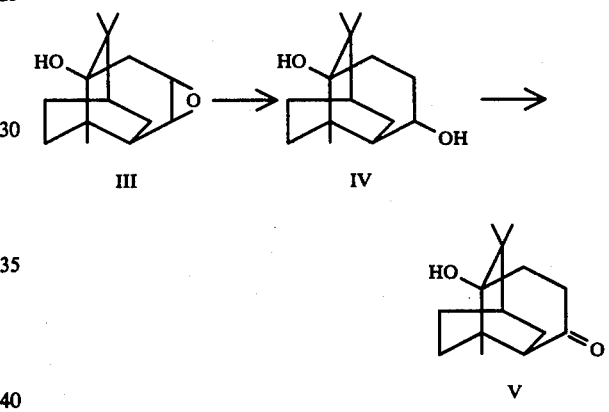

EXAMPLE 2

100 ml of anhydrous petroleum ether and 10 ml of diisobutylaluminium hydride are added to a 500 ml flask provided with stirrer, reflux condenser and dropping funnel. The reaction medium is kept under a dry nitrogen atmosphere. The 0.82 g (3.7 mmol) of the epoxyalcohol of formula III obtained according to Example 1, dissolved in 30 ml of dry petroleum ether, are added at ambient temperature to the hydride solution. After this addition, the reaction mixture is held under reflux for 3 hours, then cooled to approximately 0° C, slowly mixed with 20 ml of absolute ethyl alcohol and finally with 250 ml of saturated sodium chloride solution. The reaction mixture is extracted with petroleum ether, whereupon the organic extracts are washed to neutrality with water. Distillation of the solution produces 0.85 g of glycol of formula IV. By chromatography on silica gel, there are obtained 0.80 g of white crystallised product (ca. 82% yield) with the following constants:

Mass Spectrum: $C_{14}H_{24}O_2$ (M = 224); 224 (M); 209 (M—$CH_3$); 206 (M—$H_2O$); 191 (M—$H_2O$—$CH_3$); 188 (M—2 $H_2O$); 181 (M—$C_3H_7$); 173 (M—2 $H_2O$—$CH_3$); 163 (206—$C_3H_7$); 149 (163—$CH_3$); 145 (163—$H_2O$).

IR-Spectrum: $\nu_{max}^{KBr}$ (cm$^{-1}$): 3420; 3000; 1465; 1380–1360; 1215; 1055; 985; 935; 905.

NMR-Spectrum: (in δ units) around 1.10; 3.80.

EXAMPLE 3

0.64 g (2.86 mmol) of the glycol of formula IV obtained according to Example 2 are dissolved in 100 ml of methylene chloride. After the addition of 12 g of $CrO_3$/ pyridine complex, the mixture is stirred for 5 hours at 20°–25° C, then filtered and the filtrate taken up in ethyl ether. The solution is washed with 10% hydrochloric acid to eliminate the pyridine, with 9% bicarbonate solution and finally until neutral with water. After distillation of the solvent, there are obtained 0.60 g of red, crystallised ketoalcohol of formula V, which is purified by chromatography over silica gel. Yield 0.53 g (ca. 85%). The pure product has the following constants:

Mass Spectrum: $C_{14}H_{22}O_2$ (M = 222): 222 (M); 207 (M—$CH_3$); 2204 (M—$H_2O$); 194,189; 179 (M—$C_3H_7$).

IR-Spectrum: $\nu_{max}^{KBr}$ (cm$^{-1}$): 3460; 1700; 1420; 1385–1360; 1255; 1190; 1060–1045; 970; 775.

NMR-Spectrum: (in δ units) 0.83; 1.18 and 1.24 centred at 2.79.

Illustrative odorant compositions containing the aforesaid compound III are shown below. All parts given are by weight.

EXAMPLE 4

Soap Composition 100 parts of a conventional unperfumed toilet soap in the form of chips are mixed with 3 parts of the odorant compound of formula III to uniformly distribute said odorant compound into said soap chips.

EXAMPLE 5

| Cleansing Cream | Parts |
|---|---|
| Mineral oil | 38 |
| Beeswax | 3 |
| Spermaceti | 3 |
| Propylene glycol | 3.5 |
| Self-emulsifying higher fatty acid monoglycerides | 13 |
| Compound of formula III | 4 |
| Water | 38 |

The aforesaid composition is in form of an emulsion and is formulated in accordance with conventional procedures used in producing such emulsions.

EXAMPLE 6

| Hair Shampoo | Parts |
|---|---|
| Lauryl sodium sulfate | 10 |
| Coconut oil fatty diethanolamides | 3 |
| Compound of Example III | 2 |
| Water | 84 |

We claim:

1. The epoxyalcohol tricyclic norsesquiterpene derivative having the formula

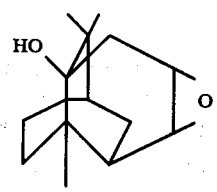

III

2. An odoriferous composition containing the derivative of claim 1.

3. An odoriferous composition according to claim 2, in the form of a cosmetic product, containing from about 1 to 20 wt.% of said derivative.

4. An odoriferous composition according to claim 2, in the form of a cleaning agent containing from about 1 to 20 wt.% of said derivative.

* * * * *